(12) United States Patent
Li et al.

(10) Patent No.: US 11,661,406 B2
(45) Date of Patent: May 30, 2023

(54) METHOD FOR PRODUCING INTERMEDIATE USEFUL FOR SYNTHESIS OF SGLT INHIBITOR

(71) Applicant: Daewoong Pharmaceutical Co., Ltd., Hwaseong-si (KR)

(72) Inventors: Qing Ri Li, Suwon-si (KR); Hee Kyoon Yoon, Cheongju-si (KR)

(73) Assignee: DAEWOONG PHARMACEUTICAL CO., LTD., Hwaseong-si (KR)

( * ) Notice: Subject to any disclaimer, the term of this patent is extended or adjusted under 35 U.S.C. 154(b) by 72 days.

(21) Appl. No.: 17/266,844

(22) PCT Filed: Aug. 9, 2019

(86) PCT No.: PCT/KR2019/010123
§ 371 (c)(1),
(2) Date: Feb. 8, 2021

(87) PCT Pub. No.: WO2020/036382
PCT Pub. Date: Feb. 20, 2020

(65) Prior Publication Data
US 2021/0292291 A1    Sep. 23, 2021

(30) Foreign Application Priority Data
Aug. 13, 2018    (KR) .................. 10-2018-0094261

(51) Int. Cl.
*C07D 307/79*    (2006.01)
(52) U.S. Cl.
CPC .................. *C07D 307/79* (2013.01)
(58) Field of Classification Search
CPC .................................................. C07D 307/79
See application file for complete search history.

(56) References Cited

U.S. PATENT DOCUMENTS 9,034,921 B2 * 5/2015 Choi .................... C07D 413/04
549/414

FOREIGN PATENT DOCUMENTS

| EP | 3056507 A1 | 8/2016 |
|---|---|---|
| EP | 3473621 A1 | 4/2019 |
| JP | 2014515396 A | 6/2014 |
| KR | 10-2014-0022086 A | 2/2014 |
| KR | 10-1770302 B1 | 8/2017 |
| KR | 10-2017-0142904 A | 12/2017 |
| WO | 2012165914 A1 | 12/2012 |
| WO | 2017217792 A1 | 12/2017 |
| WO | 2018004202 A1 | 1/2018 |

OTHER PUBLICATIONS

Extended European Search Report dated Mar. 21, 2022 in EP Application No. 19850413.6.
Office Action dated Mar. 14, 2022 in JP Application No. 2021507818.
Int'l Search Report and Written Opinion dated Nov. 14, 2019 in Int'l Application No. PCT/KR2019/010123, English translation of Int'l Search Report only.
Xu et al, "Design, Synthesis, and Biological Evaluation of Deuterated C-Aryl Glycoside as a Potent and Long-Acting Renal Sodium-Dependent Glucose Cotransporter 2 Inhibitor for the Treatment of Type 2 Diabetes," Journal of Medicinal Chemistry, vol. 57, pp. 1236-1251 (2014).
Guo et al, "The design and synthesis of novel SGLT2 inhibitors: C-glycosides with benzyltriazolopyridinone and phenylhydantoin as the aglycone moieties," Bioorganic & Medicinal Chemistry, vol. 22, pp. 3414-3422 (2014).

\* cited by examiner

*Primary Examiner* — Deepak R Rao
(74) *Attorney, Agent, or Firm* — Panitch Schwarze Belisario & Nadel LLP

(57) ABSTRACT

A method of preparing an intermediate useful for the synthesis of a diphenylmethane derivative that can be used as an SGLT inhibitor is described. A method of synthesizing a compound of Formula 7 can address problems of existing synthesis processes requiring the synthesis of the Grignard reagent and management of related substances. In addition, the method can minimize the generation of related substances, and thus does not require reprocessing of reaction products, thereby simplifying the process. Accordingly, the production yield of a diphenylmethane derivative can be maximized.

17 Claims, No Drawings

METHOD FOR PRODUCING INTERMEDIATE USEFUL FOR SYNTHESIS OF SGLT INHIBITOR

CROSS-REFERENCE TO RELATED APPLICATIONS

This application is a Section 371 of International Application No. PCT/KR2019/010123, filed Aug. 9, 2019, which was published in the Korean language on Feb. 20, 2020 under International Publication No. WO 2020/036382 A1, which claims priority under 35 U.S.C. § 119(b) to Korean Application No. 10-2018-0094261, filed on Aug. 13, 2018, the disclosures of which are incorporated herein by reference in their entireties.

TECHNICAL FIELD

The present invention relates to preparation of an intermediate useful for synthesis of a diphenylmethane derivative that can be used as an SGLT inhibitor.

BACKGROUND ART

Sodium-dependent glucose cotransporters (SGLT) cause the transport of glucose against the concentration gradient and, at same time, the transport of Na+ along the concentration gradient. Currently, two important SGLT isoforms, known as SGLT1 and SGLT2, have been cloned. SGLT1 is located in the intestine, kidney and heart, and regulates cardiac glucose transport. In addition, SGLT1 is a high-affinity, low-dose transporter and is responsible for only a fraction of renal glucose reuptake. In contrast, SGLT2 is a low-affinity, high-dose transporter that is primarily located in the apical domain of epithelial cells in the early proximal curvature tubules. In healthy individuals, more than 99% of the plasma glucose filtered by the renal glomerulus is reabsorbed and less than 1% of the total filtered glucose is excreted in the urine. It is estimated that 90% of renal glucose reuptake is facilitated by SGLT2 and the remaining 10% is mediated by SGLT1 in the late proximal rectal tubule. Genetic mutations in SGLT2 do not have a particular adverse effect on carbohydrate metabolism, but cause increased renal glucose secretion of 140 g/day depending on mutations. Human mutation studies have presumed that SGLT2 is responsible for most renal glucose reuptake, which has been considered as the subject of therapeutic studies.

Korean Patent Application Publication No. 2017-0142904 discloses a method of preparing a diphenylmethane derivative having inhibitory activity against SGLT2. This document discloses that a synthesis route is concise and a yield is improved, compared to a linear synthesis method disclosed in conventional documents, because a diphenylmethane derivative is prepared using a convergent synthesis method of individually synthesizing each major group and then coupling the same, and risk factors inherent in the linear synthesis method can be reduced.

However, the method of preparing a diphenylmethane derivative disclosed in Korean Patent Application Publication No. 2017-0142904 puts a burden on safety management due to use of heavy metals such as pyridinium chlorochromate (PCC), and requires a separate preparation process for a Grignard reagent, resulting in cost burden due to additional processes. In addition, since related substances generated in the Grignard reagent preparation process are contained also in a final product, it is necessary to manage the related substances. Further, since additional related substances are contained in a product produced after reaction between an intermediate and the Grignard reagent, there is a problem in that it is necessary to reprocess these related substances.

Therefore, there is a need for a new intermediate preparation method capable of overcoming disadvantages of existing processes.

RELATED ART DOCUMENT

Patent Document

Patent Document 1. Korean Patent Application Publication No. 2017-0142904

DISCLOSURE

Technical Problem

In accordance with an aspect of the present invention, the above and other objects can be accomplished by the provision of an improved method of preparing an intermediate useful for synthesis of a diphenylmethane derivative that can be used as an SGLT inhibitor.

Technical Solution

The present inventors have improved a process of preparing an intermediate useful for synthesis of a diphenylmethane derivative that can be used as an SGLT inhibitor.

In particular, a compound of Formula 1 that is a final target compound and an active ingredient used as an SGLT inhibitor is as follows:

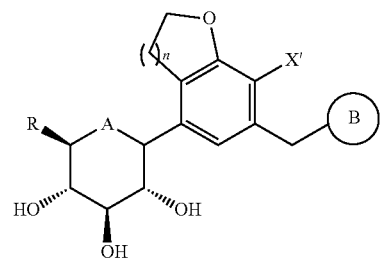

[Formula 1]

wherein A is oxygen (O) or sulfur (S),
R is hydroxymethyl or C1-7alkylthio,
n is 1 or 2,
X' is a halogen atom (for example, F, Cl, Br or I) or C1-7alkyl, and
B is

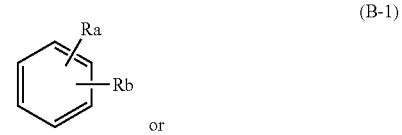

(B-1)

or

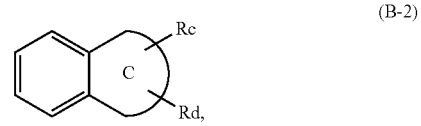

(B-2)

wherein Ra, Rb, Rc, and Rd are each independently hydrogen, halogen, hydroxy, mercapto, cyano, nitro, amino, carboxy, oxo, C1-7alkyl, C1-7alkylthio, C2-7alkenyl, C2-7alkynyl, C1-7alkoxy, C1-7alkoxy-C1-7alkyl, C2-7alkenyl-C1-7alkyloxy, C2-7alkynyl-C1-7alkyloxy, C3-10cycloalkyl, C3-7cycloalkylthio, C5-10cycloalkenyl, C3-10cycloalkyloxy, C3-10cycloalkyloxy-C1-7alkoxy, phenyl-C1-7alkyl, C1-7alkylthio-phenyl, phenyl-C1-7alkoxy, mono- or di-C1-7alkylamino, mono- or di-C1-7alkylamino-C1-7alkyl, C1-7alkanoyl, C1-7alkanoylamino, C1-7alkylcarbonyl, C1-7alkoxycarbonyl, carbamoyl, mono- or di-C1-7alkylcarbamoyl, C1-7alkylsulfonylamino, phenylsulfonylamino, C1-7alkylsulfinyl, C6-14arylsulfanyl, C6-14arylsulfonyl, C6-14aryl, 5-13 membered heteroaryl, 5-10 membered heterocycloalkyl, 5-10 membered heterocycloalkyl-C1-7alkyl, or 5-10 membered heterocycloalkyl-C1-7alkoxy;

Ring C is C3-10cycloalkyl, C5-10cycloalkenyl, C6-14aryl, 5-13 membered heteroaryl, or 5-10 membered heterocycloalkyl;

the alkyl, the alkenyl, the alkynyl and the alkoxy, each independently, are unsubstituted or have one or more substituents selected from the group consisting of halogen, hydroxy, cyano, nitro, amino, mercapto, C1-7alkyl, and C2-7alkynyl;

the cycloalkyl, the cycloalkenyl, the aryl, the heteroaryl and the heterocycloalkyl, each independently, are unsubstituted or have one or more substituents selected from the group consisting of halogen, hydroxy, cyano, nitro, amino, mercapto, C1-4alkyl, and C1-4alkoxy; and the heteroaryl and the heterocycloalkyl, each independently, contain one or more heteroatoms selected from the group consisting of N, S and O.

In an embodiment of the present invention, ring B-1 may be selected from the group consisting of:

wherein R7 is hydrogen or C1-7alkyl; and R8a and R8b are, each independently, C1-7alkyl or are linked to each other to form 5-10 membered heterocycloalkyl (containing one or more heteroatoms selected from the group consisting of N, S and O).

In another embodiment, ring B-2 may be selected from the group consisting of:

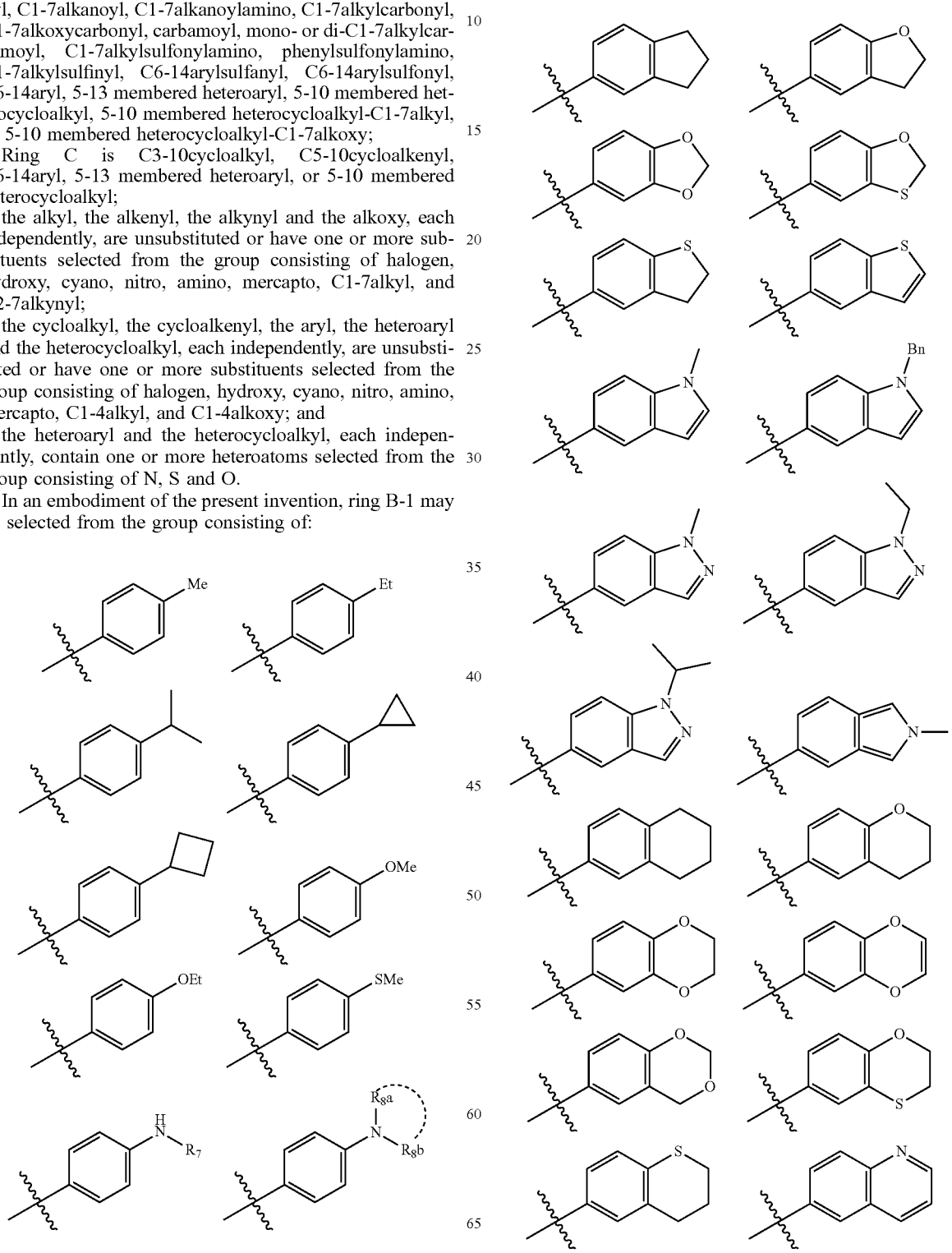

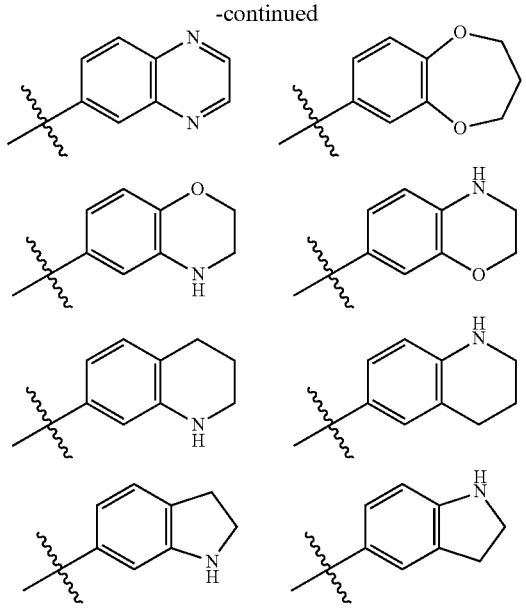

Preferably, the compound of Formula 1 may be a compound represented by Formula 1a below or a compound represented by Formula 1b below:

[Formula 1a]

[Formula 1b]

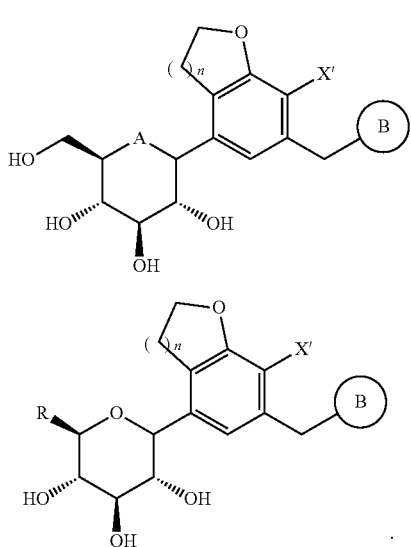

wherein A, B, X' and n are the same as those defined in Formula 1 above, and, in Formula 1b, R is C1-7alkylthio.

In accordance with a preferred embodiment of the compound of Formula 1a, A may be oxygen; n may be 1; X' may be halogen; and B may be phenyl that is unsubstituted or substituted with one or two substituents selected from the group consisting of halogen, hydroxy, cyano, nitro, amino, mercapto, C1-7alkyl, C3-10cycloalkyl, and C1-7alkoxy.

In addition, the compounds of Formulas 1a and 1b may be formed of a compound represented by Formula 8 below and a compound represented by Formula 7 below, wherein a bonding site between the compound of Formula 8 and the compound of Formula 7 (Y position) has an a-form, a β-form, or a racemic form thereof.

For example, the compound of Formula 1a may be a compound represented by Formula 1ab below:

[Formula 1ab]

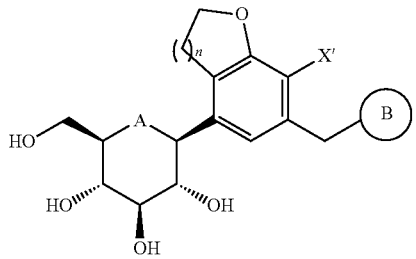

wherein A, B, n and X' are the same as those defined above.

For example, the compound of Formula 1b may be a compound represented by Formula 1bb:

[Formula 1bb]

wherein R, B, n and X' are the same as those defined above.

The present invention provides a method of preparing a compound of Formula 7, which is an intermediate, used to prepare the diphenylmethane derivative of Formula 1.

In particular, the present invention provides a method of preparing the compound of Formula 7, the method comprising:

carboxylating a compound of Formula 2 below to obtain a compound of Formula 3 below, reacting the compound of Formula 3 with oxalyl halide to obtain a compound of Formula 4 below, reacting the compound of Formula 4 with a compound of Formula 5 below to obtain a compound of Formula 6 below, and deoxygenating the compound of Formula 6 to obtain a compound of Formula 7 below:

[Formula 2]

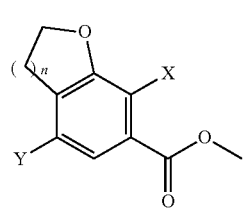

[Formula 3]

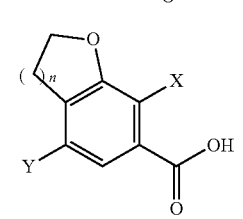

-continued

[Formula 4]
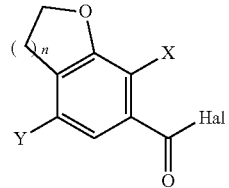

[Formula 5]
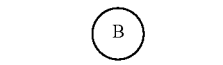

[Formula 6]

[Formula 7]
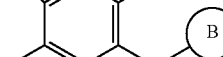

wherein
n is 1 or 2,
X, Y and Hal are each independently halogen,
X' is halogen or C1-7alkyl, and
B is

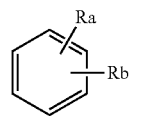

wherein Ra, Rb, Rc, and Rd are each independently hydrogen, halogen, hydroxy, mercapto, cyano, nitro, amino, carboxy, oxo, C1-7alkyl, C1-7alkylthio, C2-7alkenyl, C2-7alkynyl, C1-7alkoxy, C1-7alkoxy-C1-7alkyl, C2-7alkenyl-C1-7alkyloxy, C2-7alkynyl-C1-7alkyloxy, C3-10cycloalkyl, C3-7cycloalkylthio, C5-10cycloalkenyl, C3-10cycloalkyloxy, C3-10cycloalkyloxy-C1-7alkoxy, phenyl-C1-7alkyl, C1-7alkylthio-phenyl, phenyl-C1-7alkoxy, mono- or di-C1-7alkylamino, mono- or di-C1-7alkylamino-C1-7alkyl, C1-7alkanoyl, C1-7alkanoylamino, C1-7alkylcarbonyl, C1-7alkoxycarbonyl, carbamoyl, mono- or di-C1-7alkylcarbamoyl, C1-7alkylsulfonylamino, phenylsulfonylamino, C1-7alkylsulfinyl, C6-14arylsulfanyl, C6-14arylsulfonyl, C6-14aryl, 5-13 membered heteroaryl, 5-10 membered heterocycloalkyl, 5-10 membered heterocycloalkyl-C1-7alkyl, or 5-10 membered heterocycloalkyl-C1-7alkoxy;

Ring C is C3-10cycloalkyl, C5-10cycloalkenyl, C6-14aryl, 5-13 membered heteroaryl, or 5-10 membered heterocycloalkyl;

the alkyl, the alkenyl, the alkynyl and the alkoxy, each independently, are unsubstituted or have one or more substituents selected from the group consisting of halogen, hydroxy, cyano, nitro, amino, mercapto, C1-7alkyl, and C2-7alkynyl;

the cycloalkyl, the cycloalkenyl, the aryl, the heteroaryl and the heterocycloalkyl, each independently, are unsubstituted or have one or more substituents selected from the group consisting of halogen, hydroxy, cyano, nitro, amino, mercapto, C1-4alkyl, and C1-4alkoxy; and the heteroaryl and the heterocycloalkyl, each independently, contain one or more heteroatoms selected from the group consisting of N, S and O.

In the present specification, "halogen" refers to fluorine (F), chlorine (Cl), bromine (Br), or iodine (I).

In an embodiment,
n is 1,
X, Y and Hal are each independently halogen; and
B is

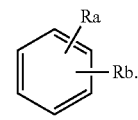

Here, a method of preparing the compound of Formula 7, wherein Ra and Rb are each independently hydrogen, halogen, hydroxy, cyano, nitro, amino, mercapto, C1-7alkyl, C3-10cycloalkyl, or C1-7alkoxy, is provided.

In a more particular embodiment, provided is a method of preparing the compound of Formula 7,
wherein n is 1,
X is chloride,
Y is bromide,
Hal is chloride, and
B is

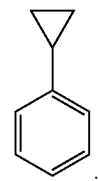

A method of synthesizing the compound of Formula 2 used as a starting material for preparing the compound of Formula 7 is disclosed in detail in Korean Patent Application Publication No. 2017-0142904.

Hereinafter, a process of synthesizing the compound of Formula 7 from the compound of Formula 2 is described in detail.

Synthesis of compound of Formula 3

[Reaction Scheme 1]

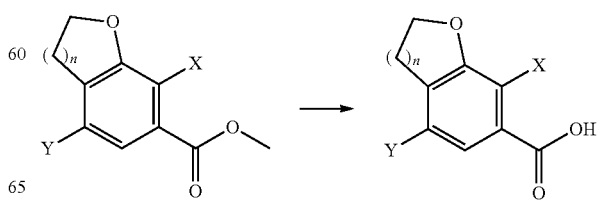

The compound of Formula 3 may be obtained by carboxylating the compound of Formula 2. This reaction may be performed, without being limited to, under a basic condition. The base may be preferably an inorganic base and may be, for example, an inorganic base such as sodium hydroxide, potassium hydroxide, lithium hydroxide, sodium carbonate, or potassium carbonate. The base may be used, without being limited to, in an amount of 2 to 4 equivalents based on 1 equivalent of the compound of Formula 2. In addition, a solvent used in the reaction is preferably a polar solvent and is, for example, C1-12 alcohol, tetrahydrofuran (THF), dioxane, acetonitrile, acetone, dimethyl sulfoxide (DMSO), dimethylformamide (DMF), or the like. The solvent may be used at a concentration of 5 to 15 v/w %. Meanwhile, a temperature condition of the reaction is not specifically limited, and the reaction may be performed, for example, at 15 to 30° C. The reaction may be performed for 1 to 3 hours, for example for 2 hours.

Synthesis of compound of Formula 4

[Reaction Scheme 2]

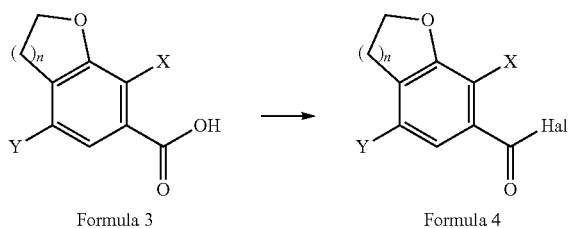

Formula 3      Formula 4

The compound of Formula 4 may be obtained by reacting the compound of Formula 3 with oxalyl halide. The generated compound represented by Formula 4 may be used in a subsequent reaction without an additional purification process.

A catalyst may be used in the reaction. This catalyst may be used in an amount of 0.01 to 0.4 equivalents based on 1 equivalent of the compound of Formula 3. An example of an applicable catalyst includes, without being limited to, N,N-dimethylformamide (DMF), N-methyl-N-phenyl-acetamide, N-methyl-N-phenyl-formamide, etc.

The oxalyl halide may be used in an amount of 0.5 to 1.5 equivalents based on 1 equivalent of the compound of Formula 3.

A reaction solvent may be, without being limited to, an aprotic solvent. An example of the aprotic solvent includes dichloromethane, dichloroethane, chloroform ($CHCl_3$), carbon tetrachloride ($CCl_4$), toluene, hexane, and ether.

The reaction may be performed, without being limited to, preferably under a nitrogen atmosphere. In addition, the reaction may be performed, without being limited to, at 0 to 30° C. The reaction may be performed for 30 minutes to 2 hours. For example, the reaction may be performed while stirring at room temperature. After the reaction, cooling may be performed at −20° C. to −10° C.

Synthesis of compound of Formula 6

[Reaction Scheme 3]

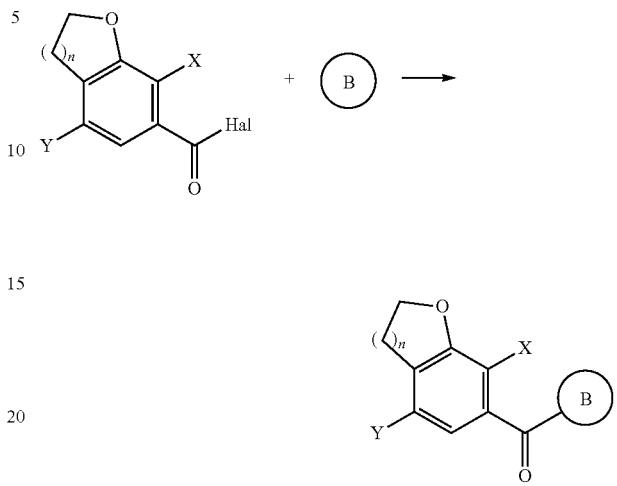

The compound of Formula 6 is prepared by reacting the compound of Formula 4 with the compound of Formula 5.

For example, the compound of Formula 5 is added to the compound of Formula 4 and stirred, and a catalyst is added to the reaction mixture and stirred, thereby preparing the compound of Formula 6.

The type of solvent applicable to the reaction is not specifically limited, and the solvent may be an aprotic solvent. For example, an example of the aprotic solvent includes dichloromethane, dichloroethane, chloroform ($CHCl_3$), carbon tetrachloride ($CCl_4$), toluene, hexane, and ether.

As the catalyst compound, Lewis acids, for example, such as $AlCl_3$, $FeCl_3$, $ZnCl_2$, $AlBr_3$, $AlI_3$, and phenylphosphonic acid (PPA), may be used, but the present invention is not limited thereto. The catalyst may be used in an amount of 0.5 to 1.5 equivalents, for example in an amount of 1.2 equivalents, based on 1 equivalent of the compound of Formula 4.

Preferably, a reaction between the compound of Formula 4 and the compound of Formula may be performed at −20° C. to −10° C., without being limited thereto. When the reaction is performed in the temperature range, there may be advantages in terms of yield and purity.

The compound of Formula 5 may be synthesized or purchased. The compound of Formula 5 may be reacted in an amount of 1.5 to 2.5 equivalents, for example in an amount of 2 equivalents, based on 1 equivalent of the compound of Formula 4, but the present invention is not limited thereto.

In Reaction Scheme 3, the compound of Formula 6 may be synthesized without use of the Grignard reagent. Accordingly, compared to existing technologies, the time and cost required to prepare the Grignard reagent can be reduced, and the generation of benzene halide-based related substances in a synthesis process of the Grignard reagent can be fundamentally prevented.

Synthesis of compound of Formula 7

[Reaction Scheme 4]

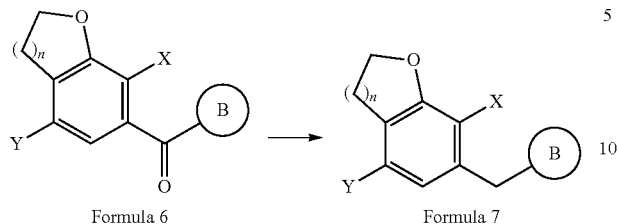

Formula 6 → Formula 7

The compound of Formula 7 is obtained by deoxygenating the compound of Formula 6. Here, triethylsilane, triisopropylsilane, t-butyldimethylsilane, sodium borohydride, or the like may be used as a reducing agent, and boron trifluoride diethylether, trimethylsilyltrifluoromethanesulfonate, aluminum chlorite, trifluoroacetic acid, trifluoromethanesulfonic acid, or the like may be used as an acid. The reducing agent may be used in an amount of 2 to 5 equivalents, more preferably in an amount of about 3 equivalents, and the acid may be used in an amount of 1.5 to 3 equivalents, more preferably in an amount of about 2 equivalents. In this case, a reaction may be performed for 2 to 5 hours at 0° C. to 250° C. In addition, as a reaction solvent, a single solvent, such as dichloromethane, 1,2-dichloroethane, or acetonitrile, or a mixed solvent, such as dichloromethane/acetonitrile (1:1) or 1,2-dichloroethane/acetonitrile (1:1), may be used.

For example, the compound of Formula 7 may be obtained by reacting the compound of Formula 6 (1.0 eq) under conditions of acetonitrile, dichloromethane (1:1, 20 v/w), boron trifluoride etherate ($BF_3 \cdot OEt_2$) (2.5 eq), triethylsilane ($Et_3SiH$) (3 eq), and 25° C.

The process of deoxygenating the compound of Formula 6 does not require a conventional step of reprocessing reaction products including related substances because the related substances are hardly generated compared to an existing process of removing a hydroxyl group (the step of removing a hydroxyl group from a compound of Formula 6a to obtain a compound of Formula 6 in Korean Patent Application Publication No. 2017-0142904).

As described above, the method of synthesizing the compound of Formula 7 according to the present invention can reduce synthesis processes, compared to existing methods, and can address problems of requiring an additional process due to synthesis of the Grignard reagent and requiring management of related substances. In addition, since the deoxygenation process of Reaction Scheme 4 can minimize generation of related substances, reprocessing of reaction products is unnecessary, thereby simplifying the process.

The compound of Formula 7 synthesized as described above may be used to prepare the compound of Formula 1.

The present invention provides a method of preparing a compound of Formula 1a, the method including:

carboxylating a compound of Formula 2 below to obtain a compound of Formula 3 below, reacting the compound of Formula 3 with oxalyl halide to obtain a compound of Formula 4 below, reacting the compound of Formula 4 with a compound of Formula 5 below to obtain a compound of Formula 6 below, deoxygenating the compound of Formula 6 to obtain a compound of Formula 7 below, and reacting the compound of Formula 7 with a compound of Formula 8 and deprotecting and reducing the same:

[Formula 1a]

[Formula 2]

[Formula 3]

[Formula 4]

[Formula 5]

[Formula 6]

[Formula 7]

[Formula 8]

wherein A is oxygen (O) or sulfur (S);
PG is a protecting group;
X' is halogen or C1-7alkyl;
n is 1 or 2;
X, Y and Hal are each independently halogen; and
B is

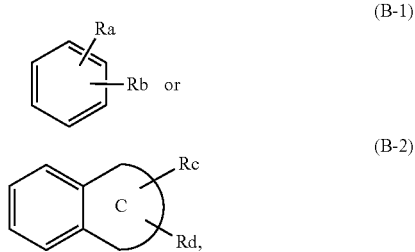

wherein Ra, Rb, Rc, and Rd are each independently hydrogen, halogen, hydroxy, mercapto, cyano, nitro, amino, carboxy, oxo, C1-7alkyl, C1-7alkylthio, C2-7alkenyl, C2-7alkynyl, C1-7alkoxy, C1-7alkoxy-C1-7alkyl, C2-7alkenyl-C1-7alkyloxy, C2-7alkynyl-C1-7alkyloxy, C3-10cycloalkyl, C3-7cycloalkylthio, C5-10cycloalkenyl, C3-10cycloalkyloxy, C3-10cycloalkyloxy-C1-7alkoxy, phenyl-C1-7alkyl, C1-7alkylthio-phenyl, phenyl-C1-7alkoxy, mono- or di-C1-7alkylamino, mono- or di-C1-7alkylamino-C1-7alkyl, C1-7alkanoyl, C1-7alkanoylamino, C1-7alkylcarbonyl, C1-7alkoxycarbonyl, carbamoyl, mono- or di-C1-7alkylcarbamoyl, C1-7alkylsulfonylamino, phenylsulfonylamino, C1-7alkylsulfinyl, C6-14arylsulfanyl, C6-14arylsulfonyl, C6-14aryl, 5-13 membered heteroaryl, 5-10 membered heterocycloalkyl, 5-10 membered heterocycloalkyl-C1-7alkyl, or 5-10 membered heterocycloalkyl-C1-7alkoxy;

Ring C is C3-10cycloalkyl, C5-10cycloalkenyl, C6-14aryl, 5-13 membered heteroaryl, or 5-10 membered heterocycloalkyl;

the alkyl, the alkenyl, the alkynyl and the alkoxy, each independently, are unsubstituted or have one or more substituents selected from the group consisting of halogen, hydroxy, cyano, nitro, amino, mercapto, C1-7alkyl, and C2-7alkynyl;

the cycloalkyl, the cycloalkenyl, the aryl, the heteroaryl and the heterocycloalkyl, each independently, are unsubstituted or have one or more substituents selected from the group consisting of halogen, hydroxy, cyano, nitro, amino, mercapto, C1-4alkyl, and C1-4alkoxy; and the heteroaryl and the heterocycloalkyl, each independently, contain one or more heteroatoms selected from the group consisting of N, S and O.

In an embodiment of the present invention, the compound of Formula 1a may have a three-dimensional structure of Formula 1ab below:

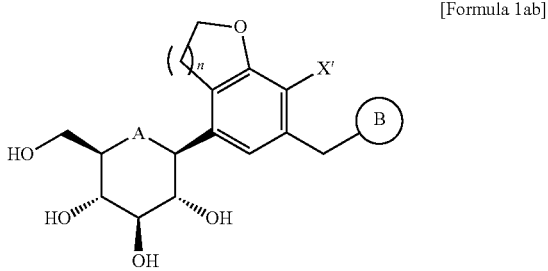

wherein A, B, n and X' are the same as those defined above.

A method of preparing the compound of Formula 1 from the compound of Formula 7 is described in detail in Korean Patent Application Publication No. 2017-0142904.

Hereinafter, processes of preparing a compound of Formula 1a and a compound of Formula 1b from the compound of Formula 7 are described.

Synthesis of Compound of Formula 1a

After reacting the compound of Formula 7 with the compound of Formula 8, a compound of Formula 1a may be prepared through deprotection and reduction processes.

A reaction between the compound of Formula 7 and the compound of Formula 8 may be performed in the presence of n-butyllithium, sec-butyllithium, t-butyllithium, i-propyl magnesium chloride (i-PrMgCl), and the like.

A compound of Formula 9a below may be obtained by reacting the compound of Formula 7 with the compound of Formula 8:

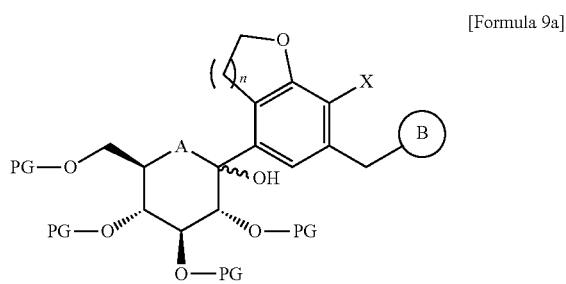

wherein A is oxygen or sulfur; n is 1 or 2; X is halogen; PG is a protecting group; and B is the same as those defined in Formula 1.

The protecting group may be, for example, a trimethylsilyl (TMS) group, a benzyl group, or an acetyl group.

Next, the compound of Formula 1a may be obtained by deprotecting the compound of Formula 9a.

For example, when the protecting group is a trimethylsilyl (TMS) group, methanesulfonic acid (CH₃SO₃H) or trimethylsilyl trifluoromethanesulfonate (TMSOTf) is added to the compound of Formula 7a to perform deprotection, thereby obtaining the compound of Formula 1a.

In addition, reduction may be additionally performed after the deprotection, thereby obtaining the compound of Formula 1a. Here, a combination of dichloromethane (CH₂Cl₂) and acetonitrile (CH₃CN) is preferred as a solvent.

The compound of Formula 1a obtained through the above steps may be a compound wherein a bonding site between the compound of Formula 8 and the compound of Formula 7 (Y position) may be an α-form or a β-form.

Accordingly, additional separation may be performed to obtain a desired α- or β-form. That is, after or during the deprotection and reduction, a process of separating only a compound wherein the bonding site between the compound of Formula 8 and the compound of Formula 7 (Y position) is a β-form may be additionally performed.

For example, a compound wherein the bonding site of the compound of Formula 8 and the compound of Formula 7 (Y position) is a β-form may be obtained by introducing a protecting group to the compound obtained as a result of the deprotection and reduction, and then isolating a precipitate generated by heating alcohol, ethyl acetate, or dichloromethane, and then deprotecting the precipitate.

In particular, a compound of Formula 9e having a β-form may be only obtained by protecting the hydroxy group of the compound obtained as a result of the deprotection and reduction with an acetyl group, etc., and then heating and stirring the same in a C1-6 alcohol solvent (methanol, ethanol or isopropanol, etc.) to isolate a precipitate:

[Formula 9e]

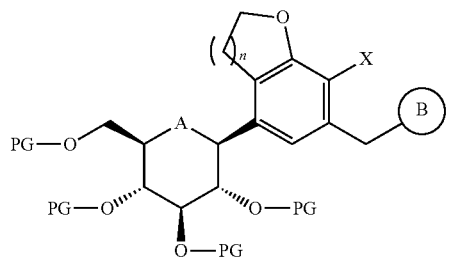

wherein A is oxygen or sulfur; n is 1 or 2; X is halogen; PG is a protecting group; and B is the same as those defined in Formula 1.

Next, the compound of Formula 9e is deprotected, thereby finally obtaining a compound of Formula 9f (0-form). Next, a compound of Formula 9g below may be obtained by performing selectively an alkylation reaction.

[Formula 9f]

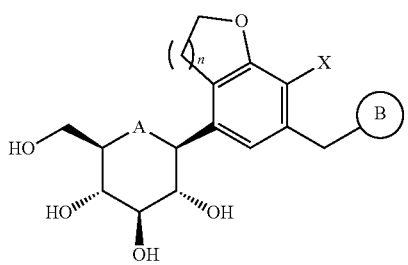

[Formula 9g]

wherein A, B, n and X' are the same as those defined in Formula 1, and Xa is C1-7alkyl.

In accordance with an embodiment of the present invention, the step of reacting the compound of Formula 7 with the compound of Formula 8 and deprotecting and reducing the same may include:

a step of reacting the compound of Formula 7 with the compound of Formula 8 in the presence of n-butyllithium, sec-butyllithium, t-butyllithium, or i-propyl magnesium chloride to obtain a compound of Formula 9a below;

a step of deprotecting and methylating the compound of Formula 9a under an acid condition in the presence of methanol to obtain a compound of Formula 9b below;

a step of reducing the compound of Formula 9b to obtain a compound of Formula 9c below; and a step of introducing a protecting group to the compound of Formula 9c and recrystallizing the same, and then deprotecting the same to obtain a compound of Formula 9f below (for example, a step of introducing a protecting group to the compound of Formula 9c, and then isolating a precipitate generated by heating the compound in alcohol, ethyl acetate, or dichloromethane, and then deprotecting the precipitate to obtain a compound of Formula 9f below):

[Formula 9a]

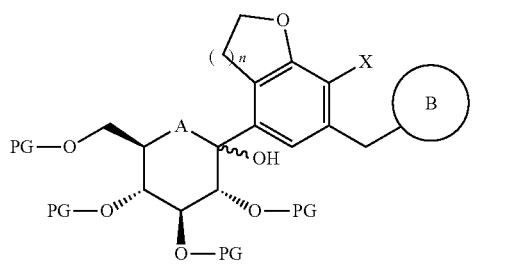

[Formula 9b]

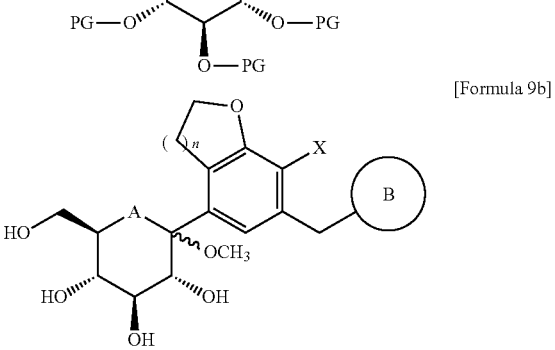

[Formula 9c]

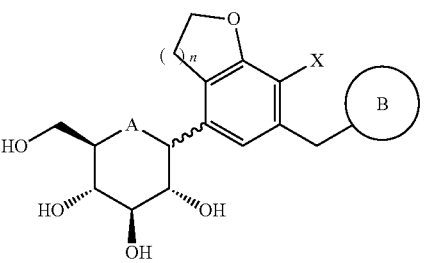

[Formula 9f]

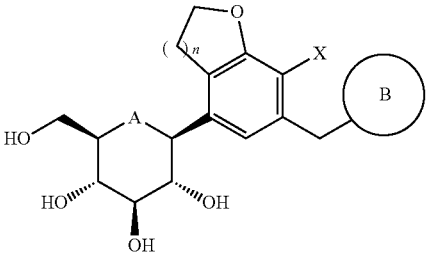

wherein PG is a protecting group; and A, B, n and X are the same as those defined in Formula 1a.

For example, the recrystallization step may be performed using a solvent selected from the group consisting of alcohol (for example, C1-6 alcohol), ethyl acetate, and dichloromethane.

After the reaction between the compound of Formula 7 and the compound of Formula 8, it is preferred to additionally perform evaporation, extraction, drying, filtration, etc. so as to obtain the compound of Formula 9a, and then use the same in a subsequent step.

An example of an acid applicable to the process of obtaining the compound of Formula 9b from the compound of Formula 9a includes hydrochloric acid, sulfuric acid, acetic acid, trifluoroacetic acid, methanesulfonic acid, trifluoromethanesulfonic acid, p-toluenesulfonic acid, hydrogen chloride gas, and the like.

In another embodiment of the present invention, the step of reacting the compound of Formula 7 with the compound of Formula 8 and deprotecting and reducing the same may include:

a step of reacting the compound of Formula 7 with the compound of Formula 8 in the presence of n-butyllithium, sec-butyllithium, t-butyllithium, or i-propyl magnesium chloride and, without separate purification, deprotect and methylating the same under an acid condition in the presence of methanol to obtain a compound of Formula 9b below;

a step of reducing the compound of Formula 9b to obtain a compound of Formula 9c below;

a step of introducing a protecting group to the compound of Formula 9c and recrystallizing the same to isolate the compound of Formula 9e; and a step of deprotecting the compound of Formula 9e to obtain a compound of Formula 9f below:

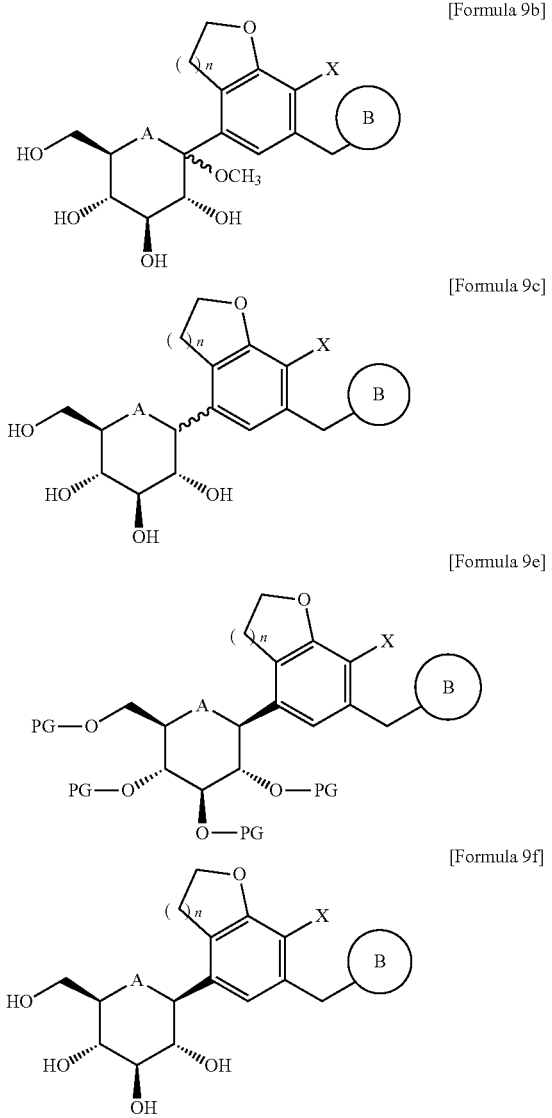

wherein PG is a protecting group; and A, B, n and X are the same as those defined in the Formula 1a.

For example, the recrystallization step may be performed using a solvent selected from the group consisting of alcohol (for example, C1-6 alcohol), ethyl acetate, and dichloromethane.

In the step of reacting the compound of Formula 7 with the compound of Formula 8, a bonding reaction is first performed. Here, based on 1 equivalent of the compound of Formula 7, the compound of Formula 8 and the reaction reagent (i.e., n-butyllithium, sec-butyllithium, t-butyllithium, or i-propyl magnesium chloride) may be respectively used in an amount of 1.5 to 2.5 equivalents, more preferably, 1.7 to 2.3 equivalents, particularly about 2.0 equivalents. This reaction may be performed at −80° C. to −10° C., more preferably −70° C. to −60° C., for 1 to 12 hours, or 1 to 3 hours. In addition, a single solvent such as tetrahydrofuran or ether, a mixed tetrahydrofuran/toluene (1:1) solvent, or the like may be used as a reaction solvent.

In addition, after the bonding reaction, deprotection and methylation reactions are performed under an acid condition. Here, an example of an applicable acid includes hydrochloric acid, sulfuric acid, acetic acid, trifluoroacetic acid, methanesulfonic acid, trifluoromethanesulfonic acid, p-toluenesulfonic acid, hydrogen chloride gas, etc. and the acid may be used in an amount of 2 to 5 equivalents, more preferably 3 equivalents, based on 1 equivalent of the compound of Formula. This reaction may be performed at 0 to 40° C., more preferably 20 to 30° C., for 6 to 24 hours, or 6 to 12 hours. In addition, methanol or the like may be used as a reaction solvent.

Next, in the step of reducing the compound of Formula 9b to obtain the compound of Formula 9c, a reduction reaction may be performed using a reducing agent and an acid. Triethylsilane, triisopropylsilane, t-butyldimethylsilane, sodium borohydride, or the like may be used as the reducing agent, and boron trifluoride diethylether, trimethylsilyltrifluoromethanesulfonate, aluminum chlorite, trifluoroacetic acid, trifluoromethanesulfonic acid, or the like may be used as the acid. The reducing agent may be used in an amount of 2 to 5 equivalents, more preferably about 3 equivalents, and the acid may be used in an amount of 1.5 to 3 equivalents, more preferably about 2 equivalents. This reaction may be performed at −50° C. to 0° C., more preferably −20° C. to −10° C., for 2 to 12 hours, or 2 to 5 hours. In addition, as a reaction solvent, a single solvent, such as dichloromethane, 1,2-dichloroethane, acetonitrile, or a mixed solvent, such as dichloromethane/acetonitrile (1:1), 1,2-dichloroethane/acetonitrile (1:1), may be used.

Next, a step of introducing a protecting group to the compound of Formula 9c to isolate only the compound (β-form) of Formula 9e and deprotecting the same is performed. At this time, a reaction using an acetylating agent and abase may be performed. An example of the acetylating agent includes acetyl chloride, acetyl bromide, acetic anhydride, and the like, and an example of the base includes sodium hydroxide, sodium carbonate, triethylamine, diisopropylethylamine, pyridine, lutidine, 4-dimethylaminopyridine, and the like. The acetylating agent may be used in an amount of 4 to 12 equivalents, more preferably about 8 equivalents, and the base may be used in an amount of 1 to 4 equivalents, more preferably about 1.5 equivalents. The reaction may be performed at 0 to 50° C., more preferably 20 to 30° C., for 1 to 12 hours, or 1 to 3 hours. In addition, acetone, ethyl acetate, tetrahydrofuran, dimethylformamide, dimethylacetamide, dichloromethane, 1,2-dichloroethane, chloroform, or the like may be used as a reaction solvent. Next, a deprotection reaction is performed. Here, a reagent such as lithium hydroxide, sodium hydroxide, potassium hydroxide, sodium methoxide, or sodium ethoxide may be used in an amount of 2 to 12 equivalents, more preferably about 5 equivalents. The reaction may be performed at 0 to 50° C., more preferably at 20 to 30° C., for 1 to 12 hours, or 1 to 3 hours. Methanol/water (1:1 to 3:1), dichloromethane/methanol (1:1 to 1:2), dichloromethane/ethanol (1:1 to 1:2), tetrahydrofuran/methanol (1:1 to 1:2), tetrahydrofuran/ethanol (1:1 to 1:2), tetrahydrofuran/methanol/water (1:1:3 to 2:1:3), tetrahydrofuran/ethanol/water (1:1:3 to 2:1:3), or the like may be used as a reaction solvent.

In accordance with another embodiment, the step of reacting the compound of Formula 7 with the compound of Formula 8 and deprotecting and reducing the same may include:

a step of reacting the compound of Formula 7 with the compound of Formula 8 in the presence of n-butyllithium, sec-butyllithium, t-butyllithium, or i-propyl magnesium chloride and deprotecting and methylating the same under an acid condition in the presence of methanol without separate purification to obtain a compound of Formula 9b below;

a step of introducing a protecting group to the compound of Formula 9b to obtain a compound of Formula 9d below;

a step of reducing the compound of Formula 9d and recrystallizing the same to isolate a compound of Formula 9e below; and a step of deprotecting the compound of Formula 9e to obtain a compound of Formula 9f below:

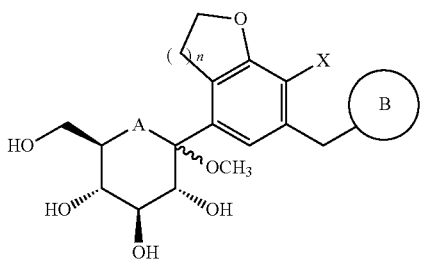

[Formula 9b]

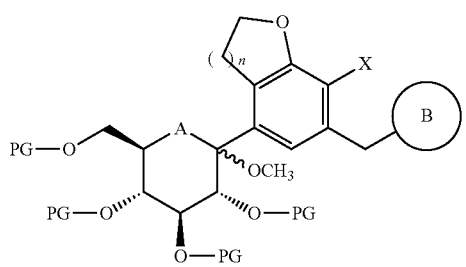

[Formula 9d]

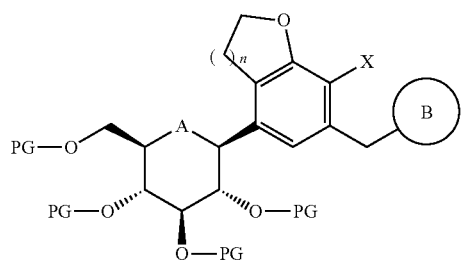

[Formula 9e]

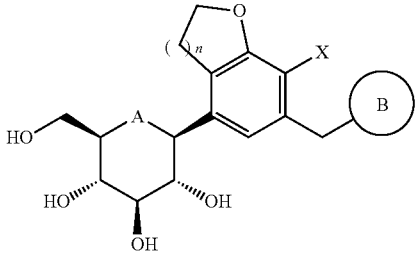

[Formula 9f]

wherein PG is a protecting group; and A, B, n and X are the same as those defined in Formula 1a.

For example, the recrystallization step may be performed using a solvent selected from the group consisting of alcohol (for example, C1-6 alcohol), ethyl acetate, and dichloromethane.

In the step of reacting the compound of Formula 7 with the compound of Formula 8 to obtain the compound of Formula 9b, a bonding reaction, a deprotection reaction, and a methylation reaction are performed. In these reactions, conditions such as a preferred equivalent ratio, reaction temperature, solvent, and the like are the same as those exemplified in the above embodiment.

In the step of introducing a protecting group to the compound of Formula 9b to obtain the compound of Formula 9d, a protecting group is introduced to the compound of Formula 9b. Here, a reaction using an acetylating agent and a base may be performed, and conditions such as a preferred acetylating agent type, base type, equivalent ratio, reaction temperature, solvent, and the like are the same as those exemplified in the above embodiment.

In the step of reducing the compound of Formula 9d and recrystallizing the same to isolate only the compound (β-form) of Formula 9e, and the step of deprotecting the compound of Formula 9e to obtain the compound of Formula 9f, a reduction reaction is first performed. Here, a reducing agent and an acid may be used, and conditions such as a preferred reducing agent type, acid type, equivalent ratio, reaction temperature, solvent, and the like are the same as those exemplified in the above embodiment.

Following the reduction reaction, a deprotection reaction is performed. Here, conditions such as a preferred reagent type, equivalent ratio, reaction temperature, solvent, and the like are the same as those exemplified in the above embodiment.

As shown in the preferred embodiments, the step of obtaining the compound of Formula 9b may be performed in two steps, or in one in-situ reaction step which is capable of further improving a final yield. In addition, when the one in-situ reaction step is performed, a crude concentrated residue containing the compound of Formula 9b may be obtained, or the compound of Formula 9b may be obtained in a solid form through crystallization and may be used in a subsequent step. In the latter case, it may be easier to improve quality and control a moisture content through removal of reaction by-products.

In addition, after synthesis of the compound of Formula 9b, the synthesized compound may be used in a subsequent step after being subjected to a purification process. For example, (i), after synthesis of the compound of Formula 9b, the synthesized compound may be mixed with an organic solvent such as toluene to form an azeotropic mixture, and then a concentration process may be repeated to remove residual moisture, thereby using an obtained residue in a subsequent step, or (ii) after synthesis of the compound of Formula 9b, crystallization may be performed, and residual moisture may be removed through vacuum drying to obtain a solid that is to be used in a subsequent step.

The present invention may also include an alkylation reaction step, after the step of reacting the compound of Formula 7 with the compound of Formula 8 and deprotecting and reducing the same.

As a result, in Formula 1, X' may be C1-7alkyl.

For example, the compound of Formula 7 may be reacted with the compound of Formula 8, and a product generated after the deprotection and reduction steps may be reacted with methylboronic acid, thereby obtaining the compound of Formula 1 (the compound of Formula 1a) wherein X' is methyl.

In addition, the compound of Formula 1a according to the present invention may be prepared in a crystalline form, an amorphous form, or a combined form thereof, but the crystalline form is preferred in that it has physicochemical properties of allowing easy formulation due to excellent stability and non-hygroscopicity.

Accordingly, the method of preparing the compound of Formula 1a according to the present invention may include, after the step of reacting the compound of Formula 7 with the compound of Formula 8 and deprotecting and reducing the same, a step of performing crystallization using various solvents to generate various crystalline forms. Korean Patent Application Publication No. 2017-0142904 discloses in detail various crystalline compounds and methods of generating the same.

As an embodiment, a solvent used in the crystallization may be selected from the group consisting of toluene; ethyl acetate; dichloromethane; acetone; acetonitrile; 2-propanol, tetrahydrofuran; n-hexane; and mixtures thereof (for example, a mixture of tetrahydrofuran and dichloromethane, and a mixture of tetrahydrofuran and n-hexane).

As another embodiment, a solvent used in the crystallization may be selected from a mixture of methanol and distilled water; a mixture of methanol and n-hexane; and a mixture of methanol, dichloromethane and n-hexane.

As still another embodiment, a solvent used in the crystallization may be selected from a mixture of ethanol, distilled water and n-hexane; and a mixture of tetrahydrofuran and toluene.

As still another embodiment, a solvent used in the crystallization may be a mixture of ethanol and n-hexane.

As a preferred embodiment, a solvent used in the crystallization may be selected from the group consisting of a mixture of toluene, ethyl acetate, dichloromethane, tetrahydrofuran, and dichloromethane, and a mixture of tetrahydrofuran and n-hexane.

The present invention also provides a method of preparing a compound of Formula 1b (in Formula 1, R=C1-7alkyl-thio, A=oxygen) below, the method including:

carboxylating a compound of Formula 2 below to obtain a compound of Formula 3 below, reacting the compound of Formula 3 with oxalyl halide to obtain a compound of Formula 4 below, reacting the compound of Formula 4 with a compound of Formula 5 to obtain a compound of Formula 6 below, deoxygenating the compound of Formula 6 to obtain a compound of Formula 7 below below, reacting the compound of Formula 7 with a compound of Formula 9 below, and then reducing the same to obtain a compound of Formula 10 below, forming a furanose ring of the compound of Formula 10 into a pyranose ring under an acidic condition, and then introducing a protecting group thereto to obtain a compound of Formula 11 below, and treating the compound of Formula 11 with thiourea and reacting the same with C1-7alkyl halide, followed by reducing the same:

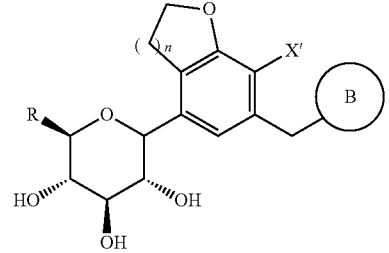

[Formula 1b]

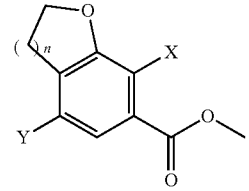

[Formula 2]

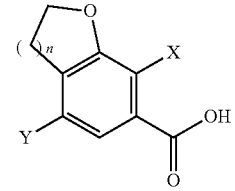

[Formula 3]

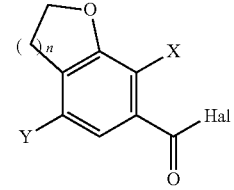

[Formula 4]

[Formula 5]

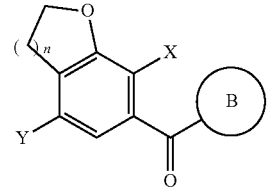

[Formula 6]

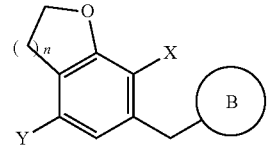

[Formula 7]

-continued

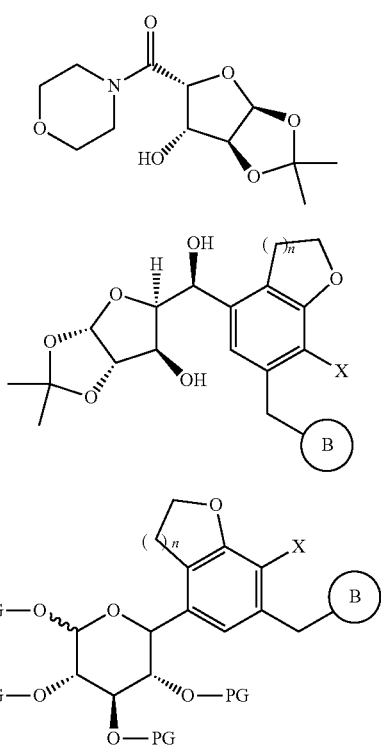

[Formula 9]

[Formula 10]

[Formula 11]

wherein A is oxygen (O) or sulfur (S);
R is C1-7alkylthio;
PG is a protecting group,
X' is halogen or C1-7alkyl;
n is 1 or 2;
X, Y and Hal are each independently halogen; and
B is

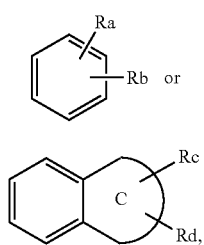

(B-1)

(B-2)

wherein Ra, Rb, Rc, and Rd are each independently hydrogen, halogen, hydroxy, mercapto, cyano, nitro, amino, carboxy, oxo, C1-7alkyl, C1-7alkylthio, C2-7alkenyl, C2-7alkynyl, C1-7alkoxy, C1-7alkoxy-C1-7alkyl, C2-7alkenyl-C1-7alkyloxy, C2-7alkynyl-C1-7alkyloxy, C3-10cycloalkyl, C3-7cycloalkylthio, C5-10cycloalkenyl, C3-10cycloalkyloxy, C3-10cycloalkyloxy-C1-7alkoxy, phenyl-C1-7alkyl, C1-7alkylthio-phenyl, phenyl-C1-7alkoxy, mono- or di-C1-7alkylamino, mono- or di-C1-7alkylamino-C1-7alkyl, C1-7alkanoyl, C1-7alkanoylamino, C1-7alkylcarbonyl, C1-7alkoxycarbonyl, carbamoyl, mono- or di-C1-7alkylcarbamoyl, C1-7alkylsulfonylamino, phenylsulfonylamino, C1-7alkylsulfinyl, C6-14arylsulfanyl, C6-14arylsulfonyl, C6-14aryl, 5-13 membered heteroaryl, 5-10 membered heterocycloalkyl, 5-10 membered heterocycloalkyl-C1-7alkyl, or 5-10 membered heterocycloalkyl-C1-7alkoxy;

Ring C is C3-10cycloalkyl, C5-10cycloalkenyl, C6-14aryl, 5-13 membered heteroaryl, or 5-10 membered heterocycloalkyl;

the alkyl, the alkenyl, the alkynyl and the alkoxy, each independently, are unsubstituted or have one or more substituents selected from the group consisting of halogen, hydroxy, cyano, nitro, amino, mercapto, C1-7alkyl, and C2-7alkynyl;

the cycloalkyl, the cycloalkenyl, the aryl, the heteroaryl and the heterocycloalkyl, each independently, are unsubstituted or have one or more substituents selected from the group consisting of halogen, hydroxy, cyano, nitro, amino, mercapto, C1-4alkyl, and C1-4alkoxy; and the heteroaryl and the heterocycloalkyl, each independently, contain one or more heteroatoms selected from the group consisting of N, S and O.

In the method of preparing the compound of Formula 1b, the step of preparing the compound of Formula 7 from the compound of Formula 2 may be performed in the same manner as in the method of preparing the compound of Formula 1a.

Hereinafter, a process of obtaining the compound of Formula 1b from the compound of Formula 7 is described:

Preparation of compound of Formula 10

[Reaction Scheme 5]

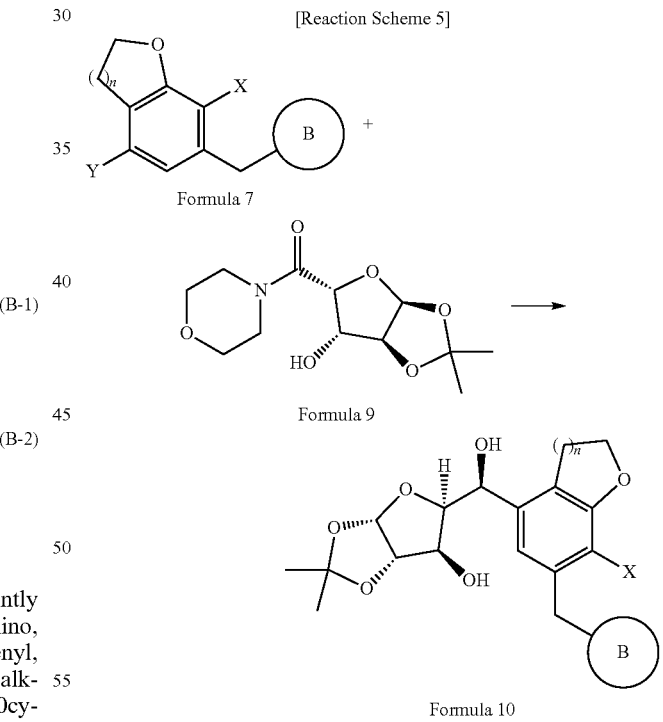

The compound of Formula 10 is obtained by reacting the compound of Formula 7 with the compound of Formula 9 and reducing the same.

The compound of Formula 9 may be prepared by a known method, e.g., a method disclosed in WO 2009/014970.

In particular, the compound of Formula 9 may be prepared according to the method disclosed in WO 2009/014970 starting from L-xylose.

In accordance with an embodiment, a compound of Formula 10a below may be obtained by reacting the compound of Formula 7 with the compound of Formula 9:

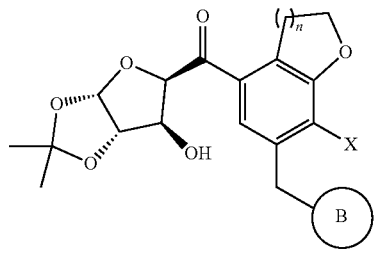

[Formula 10a]

wherein B, n and X are the same as those defined in the Formula 1.

Next, the compound of Formula 10 may be obtained by reducing the compound of Formula 10a.

Preparation of compound of Formula 11

[Reaction Scheme 6]

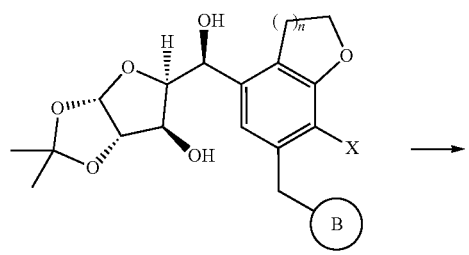

Formula 10

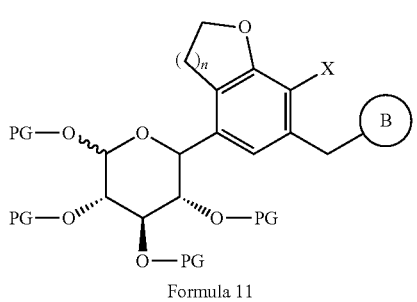

Formula 11

The compound of Formula 11 is obtained by forming a furanose ring of the compound of Formula 10 into a pyranose ring under an acidic condition, and then introducing a protecting group thereto. Through this step, a pyranose ring constituting a glucose group may be completed.

The protecting group may be, for example, an acetyl group.

Preparation of compound of Formula 12

[Reaction Scheme 7]

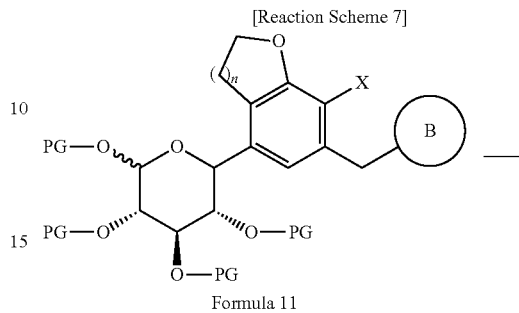

Formula 11

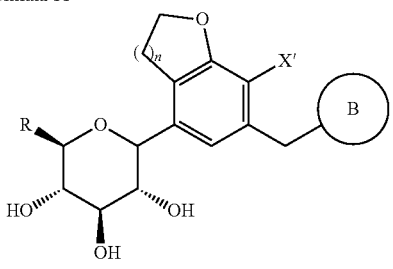

Formula 1b

The compound of Formula 11 is treated with thiourea and reacted with C1-7alkyl halide, followed by being reduced.

Through this step, an alkylthio group may be introduced to the final product (the compound of Formula 1b). The C1-7alkyl halide may be, for example, C1-7alkyl iodide.

In addition, after the step, an alkylation reaction may be additionally included. As a result, the compound of Formula 1b, wherein X' is C1-7alkyl, may be obtained.

In accordance with yet another embodiment of the present invention, a crystalline form of the compound prepared according to the above method is provided.

Advantageous Effects

A method of synthesizing a compound of Formula 7 according to the present invention can address problems of existing synthesis processes of requiring additional processes, due to synthesis of the Grignard reagent, and management of related substances. In addition, the method according to the present invention can minimize the generation of related substances, and thus does not require reprocessing of reaction products, thereby being capable of simplifying a process. Accordingly, the production yield of a diphenylmethane derivative can be maximized.

BEST MODE

Examples

Now, the present invention will be described in more detail with reference to the following examples. These examples are provided for illustrative purposes only and should not be construed as limiting the scope and spirit of the present invention.

The meanings of the abbreviations described in the following examples are as follows.

DMF: N,N-dimethylformamide
EtOH: Ethanol
Et₃SiH: Triethylsilane
MC: Dichloromethane
MC/AN: Dichloromethane and acetonitrile
NaOH: Sodium hydroxide
RT or rt: Room temperature

[Schematic reaction diagram]

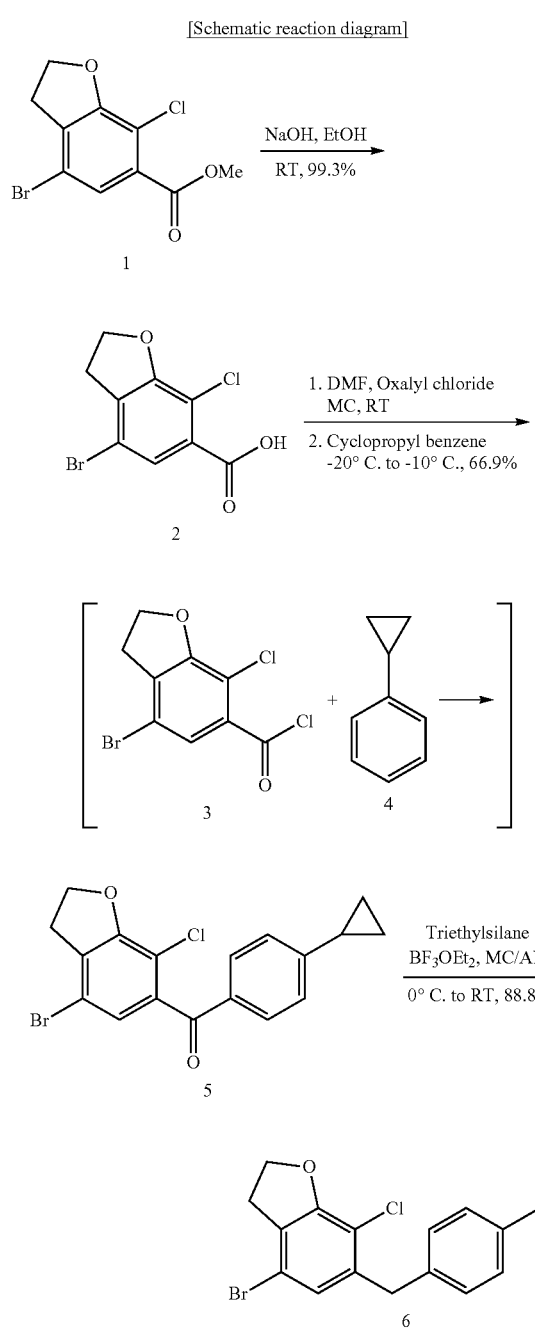

Step 1: 4-bromo-7-chloro-2,3-dihydrobenzofuran-6-carboxylic acid (Compound 2)

4 N sodium hydroxide (51.4 mL, 205.8 mmol) was added to a mixture of methyl 4-bromo-7-chloro-2,3-dihydrobenzofuran-6-carboxylate (Compound 1) (20.0 g, 68.6 mmol) in ethanol (200 mL) at room temperature. This mixture was stirred for 2 hours at room temperature, and after confirming the completion of the reaction by TLC, 1 N—HCl (acidic, pH ~1.0) was added to the reacted solution to terminate the reaction, followed by extracting EtOAc with ethyl acetate. An organic layer was dried over anhydrous magnesium sulfate, filtered, and concentrated in vacuo, thereby obtaining the title compound, Compound 2 (18.3 g, 44.4 mmol, 96.3%), in the form of a white solid. The product was used directly in a subsequent step without further purification.

¹H NMR (400 MHz, CDCl₃): δ 7.69 (s, 1H), 4.76 (t, J=9.0 Hz, 2H), 3.35 (t, J=9.0 Hz, 2H); LC-MS: [M+H]⁺ 277.

Step 2. (4-bromo-7-chloro-2,3-dihydrobenzofuran-6-yl) (4-cyclopropylphenyl)methanone (Compound 5)

DMF (0.01 mL, 0.13 mmol) was added to a solution of Compound 2 (1.00 g, 3.60 mmol) in dichloromethane (30 mL) under a nitrogen atmosphere at room temperature, and then (COCl)₂ (0.34 mL, 3.96 mmol) was added thereto dropwise. The resultant mixture was stirred at room temperature for 1 hour, and then cooled to −15° C. Next, cyclopropyl benzene (Compound 4) (0.91 mL, 7.20 mmol) was added to the reaction mixture and stirred for 5 minutes, and then AlCl₃ (0.58 g, 4.32 mmol) was added to the reaction mixture and stirred at the same temperature for 60 minutes. After confirming the completion of the reaction by TLC, an aqueous NaHCO₃ solution was added to the reaction solution to terminate the reaction, followed by extraction with ethyl acetate. An organic layer obtained through the extraction was dried over anhydrous magnesium sulfate, followed by being filtered and concentrated in vacuo. The concentrated residue was purified by silica gel chromatography, thereby obtaining the title compound, Compound 5 (1.18 g, 86.7%), in the form of a white solid.

¹H NMR (500 MHz, CDCl₃): δ 7.70 (d, J=8.0 Hz, 2H), 7.11 (d, J=8.0 Hz, 2H), 6.99 (s, 1H), 4.78 (t, J=9.0 Hz, 2H), 3.36 (t, J=7.2 Hz, 2H), 1.97-1.94 (m, 1H), 1.10-1.07 (m, 2H), 0.82-0.81 (m, 2H); LC-MS: [M+H]⁺ 377.

Step 3. 4-bromo-7-chloro-6-(4-cyclopropylbenzyl)-2,3-dihydrobenzofuran (Compound

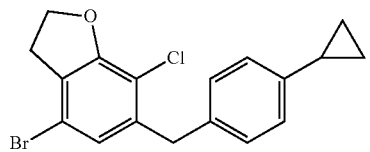 [SMILES: Clc1c(Cc2ccc(C3CC3)cc2)cc(Br)c2c1OCC2]

Et₃SiH (1.2 mL, 7.71 mmol) and BF₃-Et₂O (0.79 mL, 6.42 mmol) were sequentially added to a (4-bromo-7-chloro-2,3-dihydrobenzofuran-6-yl) (4-cyclopropylphenyl) methanone (Compound 5) (0.97 g, 2.57 mmol) solution in a mixture of dichloromethane (9.7 mL) and acetonitrile (9.7 mL) at −15° C. The reaction mixture was warmed at room temperature, and then stirred for 4 hours. After confirming the completion of the reaction by TLC, a saturated aqueous NaHCO₃ solution (40 mL) was added to the reaction solution to terminate the reaction, followed by extraction with ethyl acetate. An organic layer obtained through the extraction was dried over anhydrous magnesium sulfate, filtered, and concentrated in vacuo. The concentrated residue was purified by silica gel chromatography, thereby obtaining the title compound, Compound 6 (0.84 g, 89.9%), in the form of a gray-white solid.

¹H NMR (500 MHz, CDCl₃): δ 7.07 (d, J=10.0 Hz, 2H), 6.99 (d, J=10.0 Hz, 2H), 6.80 (s, 1H), 4.70 (t, J=11.0 Hz, 2H), 3.97 (s, 2H), 3.26 (t, J=11.0 Hz, 2H), 1.88-1.84 (m, 1H), 0.95-0.90 (m, 2H), 0.68-0.64 (m, 2H); LC-MS: [M+H]⁺ 363.

The invention claimed is:

1. A method of preparing a compound of Formula 7, the method comprising:
   carboxylating a compound of Formula 2 to obtain a compound of Formula 3,
   reacting the compound of Formula 3 with oxalyl halide to obtain a compound of Formula 4,
   reacting the compound of Formula 4 with a compound of Formula 5 to obtain a compound of Formula 6, and
   deoxygenating the compound of Formula 6 to obtain a compound of Formula 7,
   wherein the reaction between the compound of Formula 4 and the compound of Formula 5 is performed at −20° C. to −10° C.:

[Formula 2]
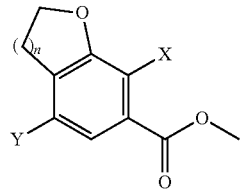

[Formula 3]
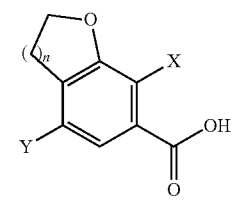

[Formula 4]
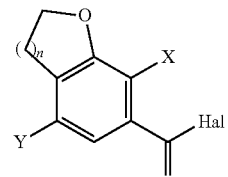

[Formula 5]

[Formula 6]
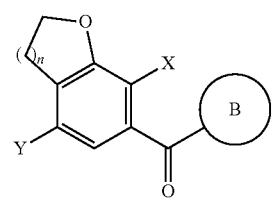

[Formula 7]
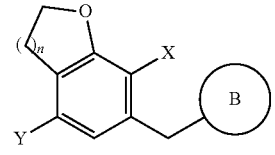

Wherein n is 1 or 2,
X, Y and Hal are each independently halogen, and
B is (B-1)
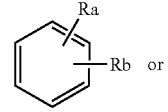

or (B-2)
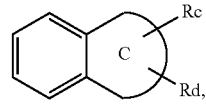

wherein Ra, Rb, Rc, and Rd are each independently hydrogen, halogen, hydroxy, mercapto, cyano, nitro, amino, carboxy, oxo, C1-7alkyl, C1-7alkylthio, C2-7alkenyl, C2-7alkynyl, C1-7alkoxy, C1-7alkoxy-C1-7alkyl, C2-7alkenyl-C1-7alkyloxy, C2-7alkynyl-C1-7alkyloxy, C3-10cycloalkyl, C3-7cycloalkylthio, C5-10cycloalkenyl, C3-10cycloalkyloxy, C3-10cycloalkyloxy-C1-7alkoxy, phenyl-C1-7alkyl, C1-7alkylthio-phenyl, phenyl-C1-7alkoxy, mono- or di-C1-7alkylamino, mono- or di-C1-7alkylamino-C1-7alkyl, C1-7alkanoyl, C1-7alkanoylamino, C1-7alkylcarbonyl, C1-7alkoxycarbonyl, carbamoyl, mono- or di-C1-7alkylcarbamoyl, C1-7alkylsulfonylamino, phenylsulfonylamino, C1-7alkylsulfinyl, C6-14arylsulfanyl, C6-14arylsulfonyl, C6-14aryl, 5-13 membered heteroaryl, 5-10 membered heterocycloalkyl, 5-10 membered heterocycloalkyl-C1-7alkyl, or 5-10 membered heterocycloalkyl-C1-7alkoxy;

Ring C is C3-10cycloalkyl, C5-10cycloalkenyl, C6-14aryl, 5-13 membered heteroaryl, or 5-10 membered heterocycloalkyl;

the alkyl, the alkenyl, the alkynyl and the alkoxy, each independently, are unsubstituted or have one or more substituents selected from the group consisting of halogen, hydroxy, cyano, nitro, amino, mercapto, C1-7alkyl, and C2-7alkynyl;

the cycloalkyl, the cycloalkenyl, the aryl, the heteroaryl and the heterocycloalkyl, each independently, are unsubstituted or have one or more substituents selected from the group consisting of halogen, hydroxy, cyano, nitro, amino, mercapto, C1-4alkyl, and C1-4alkoxy; and the heteroaryl and the heterocycloalkyl, each independently, contain one or more heteroatoms selected from the group consisting of N, S and O.

2. The method according to claim 1, wherein n is 1; X, Y and Hal are each independently halogen; and B is

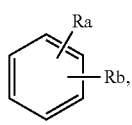
(B-1)

wherein Ra and Rb are each independently hydrogen, halogen, hydroxy, cyano, nitro, amino, mercapto, C1-7alkyl, C3-10cycloalkyl, or C1-7alkoxy.

3. The method according to claim 1, wherein n is 1, X is chloride, Y is bromine, Hal is chloride, and B is

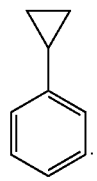

4. The method according to claim 1, wherein the deoxygenating the compound of Formula 6 to obtain a compound of Formula 7 is performed at 0° C. to 25° C.

5. The method according to claim 1, wherein the compound of Formula 4 is obtained by reacting the compound of Formula 3 with oxalyl halide in the presence of a catalyst.

6. The method according to claim 5, wherein the catalyst is used in an amount of 0.01 to 0.4 equivalents based on 1 equivalent of the compound of Formula 3.

7. A method of preparing a compound of Formula 1a, the method comprising:
carboxylating a compound of Formula 2 to obtain a compound of Formula 3,
reacting the compound of Formula 3 with oxalyl halide to obtain a compound of Formula 4,
reacting the compound of Formula 4 with a compound of Formula 5 to obtain a compound of Formula 6,
deoxygenating the compound of Formula 6 to obtain a compound of Formula 7, and
reacting the compound of Formula 7 with a compound of Formula 8 and deprotecting and reducing the same, wherein the reaction between the compound of Formula 4 and the compound of Formula 5 is performed at −20° C. to −10° C.:

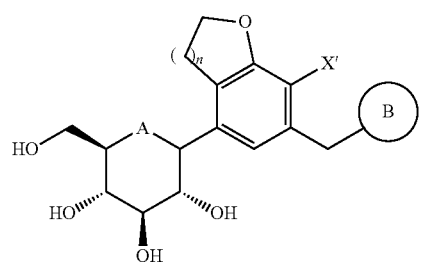
[Formula 1a]

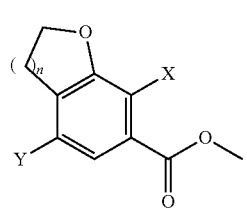
[Formula 2]

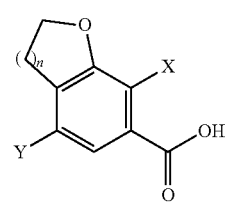
[Formula 3]

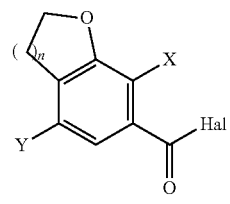
[Formula 4]

[Formula 5]

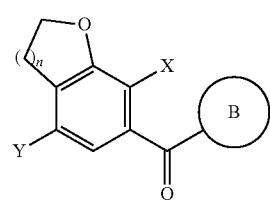
[Formula 6]

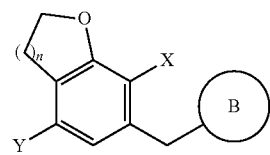
[Formula 7]

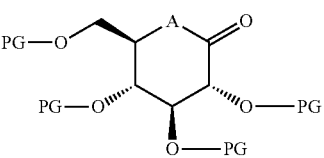
[Formula 8]

wherein A is oxygen (O) or sulfur (S);
PG is a protecting group,
X' is halogen or C1-7alkyl;
n is 1 or 2,
X, Y and Hal are each independently halogen; and
B is

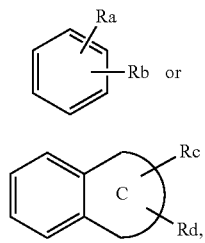

wherein Ra, Rb, Rc, and Rd are each independently hydrogen, halogen, hydroxy, mercapto, cyano, nitro, amino, carboxy, oxo, C1-7alkyl, C1-7alkylthio, C2-7alkenyl, C2-7alkynyl, C1-7alkoxy, C1-7alkoxy-C1-7alkyl, C2-7alkenyl-C1-7alkyloxy, C2-7alkynyl-C1-7alkyloxy, C3-10cycloalkyl, C3-7cycloalkylthio, C5-10cycloalkenyl, C3-10cycloalkyloxy, C3-10cycloalkyloxy-C1-7alkoxy, phenyl-C1-7alkyl, C1-7alkylthio-phenyl, phenyl-C1-7alkoxy, mono- or di-C1-7alkylamino, mono- or di-C1-7alkylamino-C1-7alkyl, C1-7alkanoyl, C1-7alkanoylamino, C1-7alkylcarbonyl, C1-7alkoxycarbonyl, carbamoyl, mono- or di-C1-7alkylcarbamoyl, C1-7alkylsulfonylamino, phenylsulfonylamino, C1-7alkylsulfinyl, C6-14arylsulfanyl, C6-14arylsulfonyl, C6-14aryl, 5-13 membered heteroaryl, 5-10 membered heterocycloalkyl, 5-10 membered heterocycloalkyl-C1-7alkyl, or 5-10 membered heterocycloalkyl-C1-7alkoxy;

Ring C is C3-10cycloalkyl, C5-10cycloalkenyl, C6-14aryl, 5-13 membered heteroaryl, or 5-10 membered heterocycloalkyl;

the alkyl, the alkenyl, the alkynyl and the alkoxy, each independently, are unsubstituted or have one or more substituents selected from the group consisting of halogen, hydroxy, cyano, nitro, amino, mercapto, C1-7alkyl, and C2-7alkynyl;

the cycloalkyl, the cycloalkenyl, the aryl, the heteroaryl and the heterocycloalkyl, each independently, are unsubstituted or have one or more substituents selected from the group consisting of halogen, hydroxy, cyano, nitro, amino, mercapto, C1-4alkyl, and C1-4alkoxy; and the heteroaryl and the heterocycloalkyl, each independently, contain one or more heteroatoms selected from the group consisting of N, S and O.

8. The method according to claim 7, wherein, after the deprotecting and reducing, an alkylation reaction is additionally comprised, and
X' is C1-7alkyl.

9. The method according to claim 7, wherein the compound of Formula 1a has a three-dimensional structure of Formula 1ab below:

[Formula 1ab]

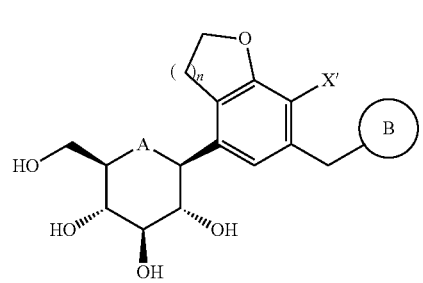

wherein A, B, n and X' are the same as those defined in claim 7.

10. The method according to claim 7, wherein the reacting of the compound of Formula 7 with a compound of Formula 8 and the deprotecting and reducing the same comprises:

reacting the compound of Formula 7 with the compound of Formula 8 in the presence of n-butyllithium, sec-butyllithium, t-butyllithium, or i-propyl magnesium chloride to obtain a compound of Formula 9a;

deprotecting and methylating the compound of Formula 9a under an acid condition in the presence of methanol to obtain a compound of Formula 9b;

reducing the compound of Formula 9b to obtain a compound of Formula 9c; and introducing a protecting group to the compound of Formula 9c and recrystallizing the same, followed by deprotection, thereby obtaining a compound of Formula 9f:

[Formula 9a]

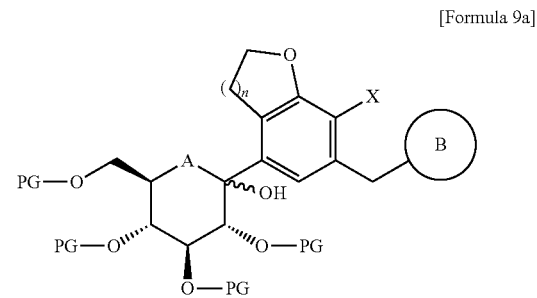

[Formula 9b]

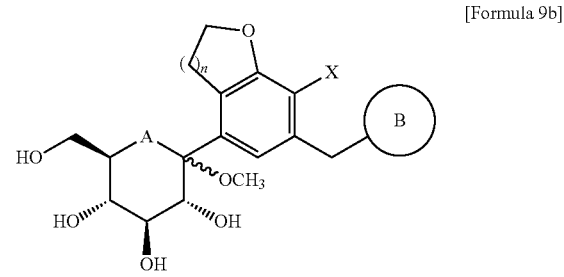

[Formula 9c]

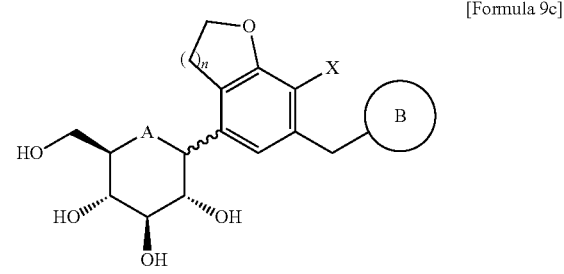

[Formula 9f]

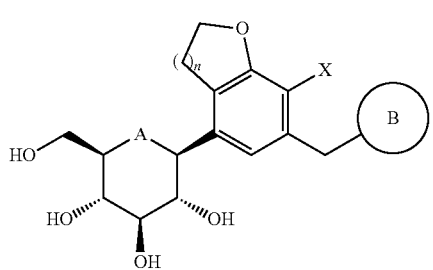

wherein PG is a protecting group; and A, B, n and X are the same as those defined in claim 7.

11. The method according to claim 7, wherein the reacting of the compound of Formula 7 with the compound of Formula 8 and the deprotecting and reducing the same comprises:

reacting the compound of Formula 7 with the compound of Formula 8 in the presence of n-butyllithium, sec-butyllithium, t-butyllithium, or i-propyl magnesium chloride and deprotect and methylating the same under an acid condition in the presence of methanol without separate purification to obtain a compound of Formula 9b;

reducing the compound of Formula 9b to obtain a compound of Formula 9c;

introducing a protecting group to the compound of Formula 9c and recrystallizing the same to isolate the compound of Formula 9e; and deprotecting the compound of Formula 9e to obtain a compound of Formula 9f:

[Formula 9b]

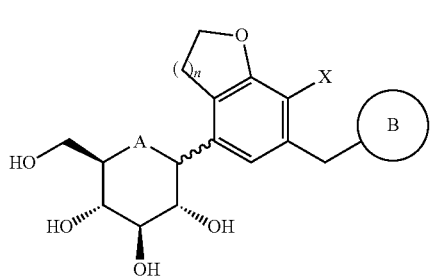

[Formula 9c]

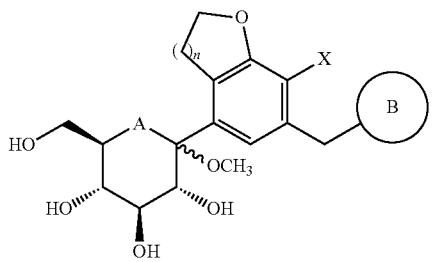

[Formula 9e]

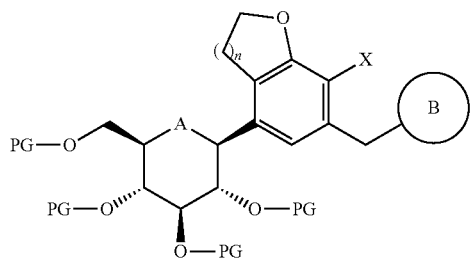

[Formula 9f]

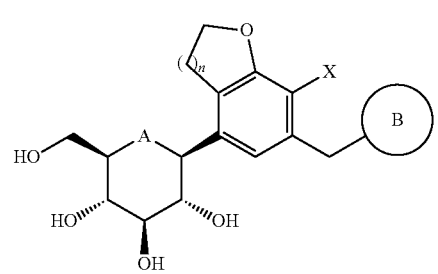

wherein PG is a protecting group; and A, B, n and X are the same as those defined in claim 7.

12. The method according to claim 7, wherein the reacting of the compound of Formula 7 with the compound of Formula 8 and the deprotecting and reducing the same comprises:

reacting the compound of Formula 7 with the compound of Formula 8 in the presence of n-butyllithium, sec-butyllithium, t-butyllithium, or i-propyl magnesium chloride and deprotecting and methylating the same under an acid condition in the presence of methanol without separate purification to obtain a compound of Formula 9b;

introducing a protecting group to the compound of Formula 9b to obtain a compound of Formula 9d; and reducing and recrystallizing the compound of Formula 9d to isolate a compound of Formula 9e; and deprotecting the compound of Formula 9e to obtain a compound of Formula 9f:

[Formula 9b]

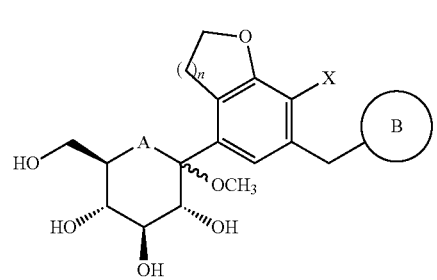

-continued

[Formula 9d]
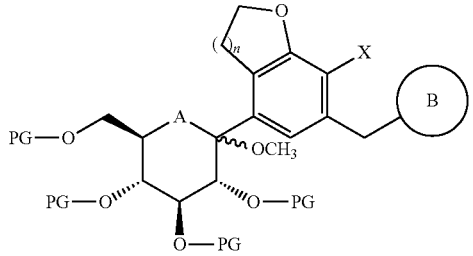

[Formula 9e]
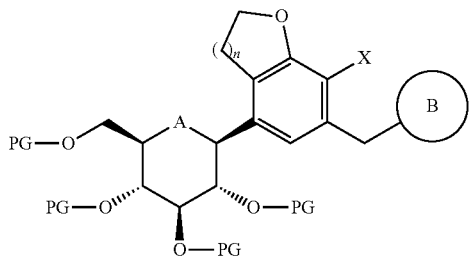

[Formula 9f]
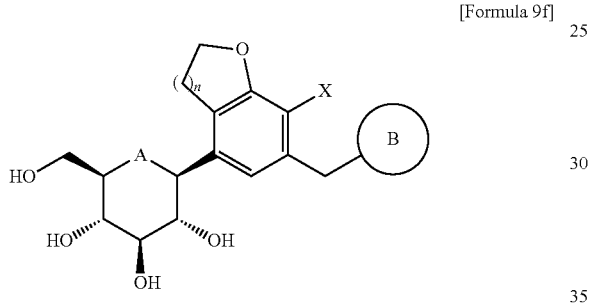

wherein PG is a protecting group; and A, B, n and X are the same as those defined in claim 7.

13. The method according to claim 10, wherein the compound of Formula 8 and n-butyllithium are respectively used in an amount of 1.5 to 2.5 equivalents based on 1 equivalent of the compound of Formula 7.

14. The method according to claim 10, wherein the recrystallizing is performed using a solvent selected from the group consisting of alcohol, ethyl acetate, and dichloromethane.

15. The method according to claim 7, wherein n is 1.

16. The method according to claim 7, wherein A is oxygen;
n is 1;
X' is halogen; and
B is phenyl unsubstituted or substituted with one or two substituents selected from the group consisting of halogen, hydroxy, cyano, nitro, amino, mercapto, C1-7alkyl, C3-10cycloalkyl, and C1-7alkoxy.

17. A method of preparing a compound of Formula 1b, the method comprising:
carboxylating a compound of Formula 2 to obtain a compound of Formula 3,
reacting the compound of Formula 3 with oxalyl halide to obtain a compound of Formula 4,
reacting the compound of Formula 4 with a compound of Formula 5 to obtain a compound of Formula 6,
deoxygenating the compound of Formula 6 to obtain a compound of Formula 7,
reacting the compound of Formula 7 with the compound of Formula 9, and then reducing the same to obtain a compound of Formula 10,
forming a furanose ring of the compound of Formula 10 into a pyranose ring under an acidic condition, and then introducing a protecting group thereto to obtain a compound of Formula 11, and
treating the compound of Formula 11 with thiourea and reacting the same with C1-7alkyl halide, followed by reducing the same,
wherein the reaction between the compound of Formula 4 and the compound of Formula 5 is performed at −20° C. to −10° C.:

[Formula 1b]
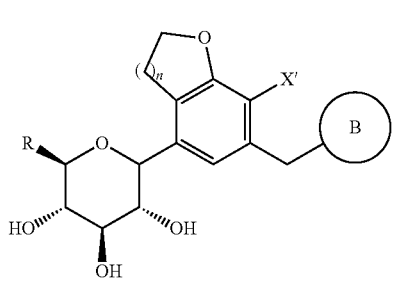

[Formula 2]
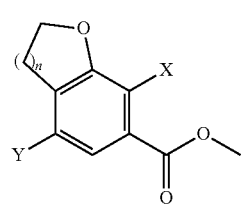

[Formula 3]
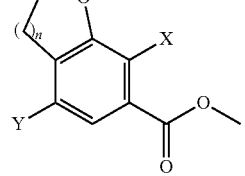

[Formula 4]
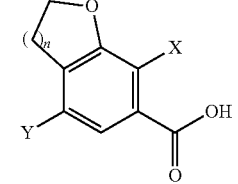

[Formula 5]
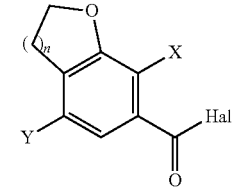

[Formula 6]
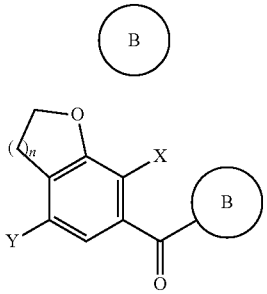

[Formula 7]
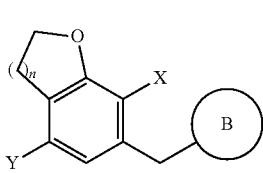

-continued

[Formula 9]

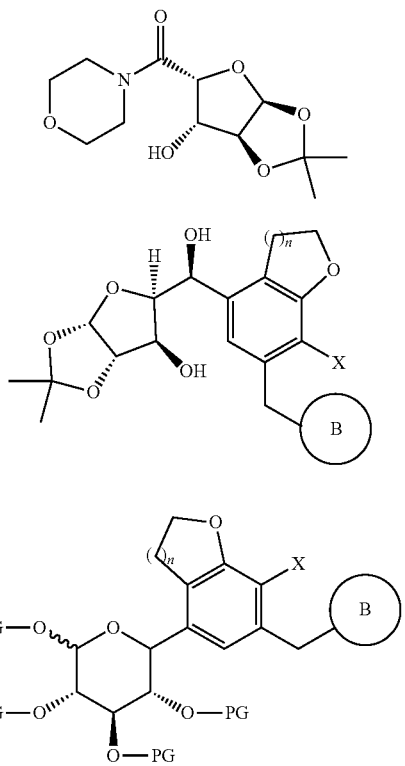

[Formula 10]

[Formula 11]

wherein
R is C1-7alkylthio;
PG is a protecting group,
X' is halogen or C1-7alkyl;
n is 1 or 2;
X, Y and Hal are each independently halogen; and
B is

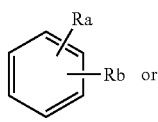

(B-1)

-continued

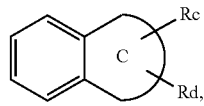

(B-2)

wherein Ra, Rb, Rc, and Rd are each independently hydrogen, halogen, hydroxy, mercapto, cyano, nitro, amino, carboxy, oxo, C1-7alkyl, C1-7alkylthio, C2-7alkenyl, C2-7alkynyl, C1-7alkoxy, C1-7alkoxy-C1-7alkyl, C2-7alkenyl-C1-7alkyloxy, C2-7alkynyl-C1-7alkyloxy, C3-10cycloalkyl, C3-7cycloalkylthio, C5-10cycloalkenyl, C3-10cycloalkyloxy, C3-10cycloalkyloxy-C1-7alkoxy, phenyl-C1-7alkyl, C1-7alkylthio-phenyl, phenyl-C1-7alkoxy, mono- or di-C1-7alkylamino, mono- or di-C1-7alkylamino-C1-7alkyl, C1-7alkanoyl, C1-7alkanoylamino, C1-7alkylcarbonyl, C1-7alkoxycarbonyl, carbamoyl, mono- or di-C1-7alkylcarbamoyl, C1-7alkylsulfonylamino, phenylsulfonylamino, C1-7alkylsulfinyl, C6-14arylsulfanyl, C6-14arylsulfonyl, C6-14aryl, 5-13 membered heteroaryl, 5-10 membered heterocycloalkyl, 5-10 membered heterocycloalkyl-C1-7alkyl, or 5-10 membered heterocycloalkyl-C1-7alkoxy;

Ring C is C3-10cycloalkyl, C5-10cycloalkenyl, C6-14aryl, 5-13 membered heteroaryl, or 5-10 membered heterocycloalkyl;

the alkyl, the alkenyl, the alkynyl and the alkoxy, each independently, are unsubstituted or have one or more substituents selected from the group consisting of halogen, hydroxy, cyano, nitro, amino, mercapto, C1-7alkyl, and C2-7alkynyl;

the cycloalkyl, the cycloalkenyl, the aryl, the heteroaryl and the heterocycloalkyl, each independently, are unsubstituted or have one or more substituents selected from the group consisting of halogen, hydroxy, cyano, nitro, amino, mercapto, C1-4alkyl, and C1-4alkoxy; and the heteroaryl and the heterocycloalkyl, each independently, contain one or more heteroatoms selected from the group consisting of N, S and O.

\* \* \* \* \*